United States Patent [19]

Hallcher

[11] Patent Number: 4,740,617
[45] Date of Patent: Apr. 26, 1988

[54] SORBIC ACID PROCESS WITH CRYSTALLIZATION

[75] Inventor: Richard C. Hallcher, Maryland Heights, Mo.

[73] Assignee: Monsanto Company, St. Louis, Mo.

[21] Appl. No.: 332,391

[22] Filed: Dec. 21, 1981

[51] Int. Cl.[4] .................. C07C 51/377; C07C 57/10
[52] U.S. Cl. .................................. 562/599; 562/600; 562/601
[58] Field of Search .................. 562/599, 600, 601

[56] References Cited

U.S. PATENT DOCUMENTS 3,992,442  11/1976  Kageyama et al. .............. 562/601
4,022,822  5/1977  Tsujino et al. .................. 562/601

Primary Examiner—Vivian Garner
Attorney, Agent, or Firm—Linda L. Lewis; James W. Williams, Jr.

[57] ABSTRACT

Preparation of sorbic acid from precursors by contact with acid catalysts is improved by utilizing crystallization to separate sorbic acid during the preparation.

21 Claims, 1 Drawing Sheet

SORBIC ACID PROCESS WITH CRYSTALLIZATION

The present invention concerns processes for preparing sorbic acid. In particular it concerns processes for converting precursors such as γ-vinyl-γ-butyrolactone or acyloxy hexenoic acids to sorbic acid with high selectivity.

BACKGROUND OF THE INVENTION

It is known that γ-vinyl-γ-butyrolactone can be converted to sorbic acid by contact with various acids or catalyts; see U.S. Pat. Nos. 4,022,822 and 4,158,741. Also the present applicant and co-applicants have shown that acetoxyhexenoic acids can be converted to sorbic acid by acid catalysts, as disclosed in copending application Ser. No. 222,200 filed Jan. 2, 1981 U.S. Pat. No. 4,356,317.

SUMMARY OF THE INVENTION

The present invention involves converting γ-vinyl-γ-butyrolactone or acetoxyhexenoic acids or other sorbic acid precursors to sorbic acid in a procedure in which the concentration of sorbic acid in the reaction medium is kept at a low value. In another aspect, it involves converting sorbic acid precursors to sorbic acid while the sorbic acid is removed from the reaction medium by crystallization, as in a continuous synthesis process with continuous removal of sorbic acid product. In still another aspect, the invention involves isomerization of hexadienoic acids to sorbic acid with continuous separation and recovery of the sorbic acid, particularly by crystallization. Another feature of the invention is the use of very low concentrations of lactone or acetoxyhexenoic acids in the conversion to sorbic acid.

DETAILED DESCRIPTION OF THE INVENTION

In the present process, precursors can be gradually converted to sorbic acid, and the sorbic acid can be selectively removed from the reaction medium by crystallization, thereby improving selectivity to sorbic acid by preventing further reaction or degradation of the sorbic acid product. The process is conveniently effected by cycling a medium containing the sorbic acid precursor between a reaction stage or zone and a crystallization stage or zone. The reaction zone involves contact with a conversion catalyst at elevated temperature, while the crystallization zone involves cooling to effect crystallization and separation of the crystals.

Figure 1:
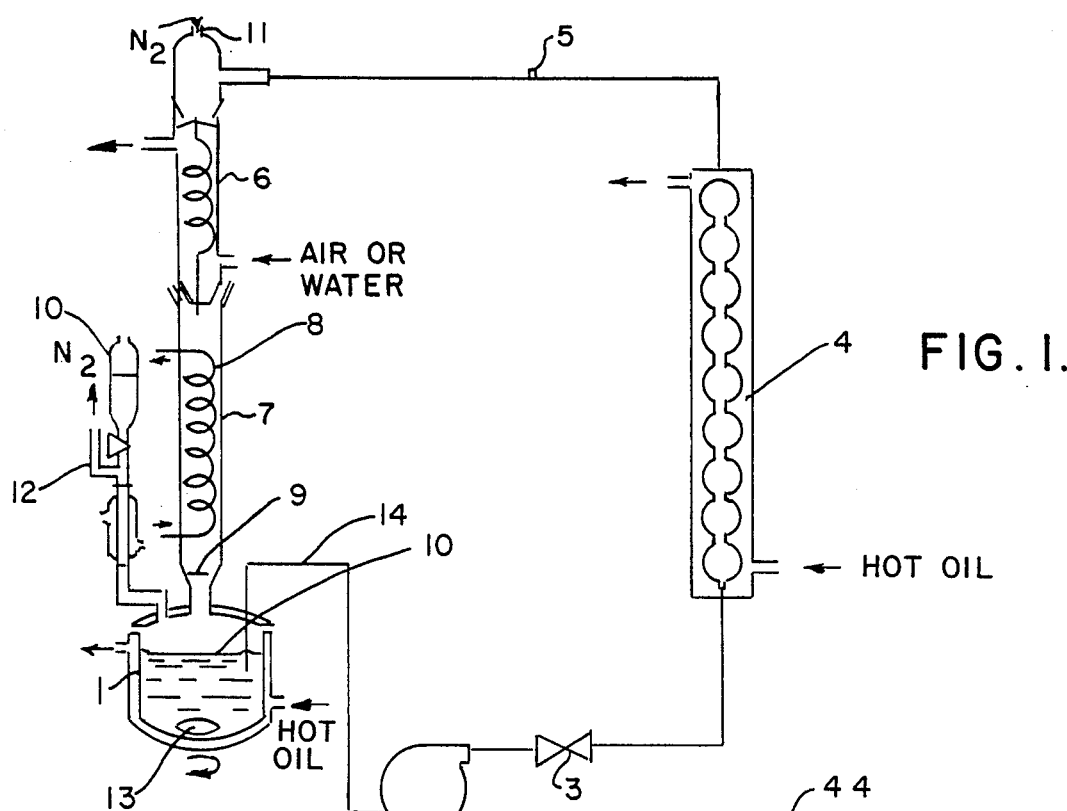
FIG. 1 illustrates an apparatus for effecting the reaction in and crystallization from an organic solvent, employing an insoluble resin catalyst.

The procedures for converting precursors to sorbic acid referred to hereinabove, generally involving elevated temperature and acid catalyst, can be utilized in the present invention, along with the improvement described herein for removing the sorbic acid from the reaction medium by crystallization to improve the selectivity to sorbic acid. Thus, the acid contact in the present process is generally conducted at elevated temperature in order to promote the reaction, although the formation of sorbic acid occurs to some extent at ambient temperatures. The contact of the lactone or other precursor will generally be carried out at temperatures from about 30° to about 150° or 200° C., preferably from about 60° to about 140° C. Operation in the range of about 80° to 110° gives fairly good reaction rates. If necessary, pressurized equipment can be used to avoid loss of reaction components or solvent, but it will often be more convenient to operate below the boiling point of the components or reaction mixture involved, or possibly at reflux conditions. Strong acids in general can be used in the present invention, e.g. mineral acids, aromatic sulfonic acids, aliphatic sulfonic acids, etc., such as hydrochloric acid, sulfuric acid, phosphoric acid, p-toluenesulfonic acid, methane sulfonic acid, etc. Acidic ion exchange resins can be used, particularly strongly acidic ion exchange resins, e.g. sulfonic acid type resins. Examples of useful ion exchange resins include the ion exchange resins, Amberlyst 15, Amberlyst XN 1005, Amberlyst XN 1010, Amberlite IR-120B, all strongly acidic cation exchange resins, particularly polystyrenes with acidic groups, e.g. sulfonate groups ($-SOH_3H$), and by Rohm and Haas Company under the foregoing trademarks; Nafion ® N-501, a sulfonated polyfluoroether polymer; and Dowex ® 50WX8 polymer, a styrene-divinylbenzene copolymer with acidic groups. Also such mineral acids as hydrochloric, phosphoric and sulfonic acids. It will be recognized that the various other catalysts can be used to supply the hydrogen ion for catalysis of the reaction. Good conversions and selectivities are obtained with some ion exchange resins. In addition the ion exchange resins have the advantage of not dissolving in the acetoxy-acids or their solvent, and present the possibility of more convenient separation from the sorbic acid product.

The Amberlite ® and Amberlyst ® ion exchange resins are further described as composed of long chains of polystyrene locked together by means of divinylbenzene crosslinks into a three dimensional, insoluble matrix. The acidic resins have sulfonic acid groups bonded to the matrix. The Amberlyst ® 15 resin is macroporous, and referred to as macroreticular. Amberlyst 15 ® is described as having a weight capacity as dry resin of 4.40 milliequivalent gram and a calculated weight capacity as internal surface of 0.193 milliequivalent/gram; and internal surface area, 55 square meters/gram, porosity of 36% and average pore diameter of 265. Angstroms. The function of the acids is apparently to supply hydrogen ion which catalyzes the conversion to sorbic acid. Also, it will often be advantageous to use a copper or other catalyst in conjunction with the acid, as illustrated herein, and as further described in a simultaneously filed copending application Ser. No. 332,393, of the present applicant and another.

The use of crystallization in the present process to remove the sorbic acid product appears to be beneficial because of the propensity of the sorbic acid to degrade or undergo further reaction. Therefore the invention will be useful in processes for conversion of various precursors to sorbic acid through acid catalysis, in general without regard as to the particular precursor. Precursors which can be used include γ-vinyl-γ-butyrolactone, acyloxyhexenoic acids, and polyester. The acyloxyhexenoic acids include particularly 6-acetoxy-4-hexenoic acid and 4-acetoxy-5-hexenoic acids, individually or as mixtures. Also other acyloxy groups can be present in such compounds in place of the acetoxy groups, particularly acyloxy moieties from lower alkanoic acids, such as those with 2 to 6 or so carbon atoms. Also any compounds which isomerize or react under the reaction conditions used herein to form the described lactone or acyloxyhexenoic acids, can be used as precursors in the present process. Thus hydroxy or other substituted hexenoic acids may isomerize to γ-vinyl-γ-butyrolactone under the reaction conditions and serve as precursors in the present process. A polyester useful herein is the polyester of 3-hydroxy-4-hexenoic acid, and is obtained by the reaction of ketene and crotonaldehyde in a known industrial process for producing sorbic acid. Treatment with hydrochloric acid is a known method for converting it to sorbic acid. Another precursor is 5-hydroxy-3-hexenoic acid lactone. In general the reactions producing sorbic acid in the present process will be mainly rearrangement or isomerization reactions involving possibly ring opening, hydrolysis, deacylation, dehydration; olefinic bond isomerization, etc.

FIG. 1 illustrates a convenient laboratory apparatus for continuous preparation of sorbic acid with continuous crystallization of the sorbic acid. A jacketed resin kettle 1 contains the sorbic acid precursor, e.g. γ-vinyl-γ-butyrolactone or acetoxyhexenoic acids, in a solvent, e.g. a hydrocarbon. The vessel is heated by circulation of hot oil through the jacket. An exit line 14 i.e. tube, with inlet below the liquid surface 10 in the vessel leads to a magnetically driven centrifugal pump 2 and then through control valve 3 to a jacketed column 4 containing a fluidized acidic ion exchange resin bed. The column is heated by circulation of hot oil through the jacket. A line from the top of column 4 leads past sampling septum 5 to the top of a column comprised of a precooler section 6 and crystallization section 7. Air or water can be utilized for precooling in 6 while a refrigerated coolant, such as ethylene glycol is carried through the cooling coil 8 in 7. A porous frit or filter 9 is at the bottom of 7. An addition funnel 10 is provided for addition of material to be reacted, or other components. A nitrogen inlet 11 is provided at the top of the pre-cooler, crystallizer column, and a nitrogen exit 12 below the addition funnel. In operation the sorbic precursor and solvent are heated to approximately the desired reaction temperature in the kettle 1, circulated to and through the resin bed in 4 where additional heat is provided for temperature control. The reaction stream is then circulated through the coil in pre-cooler 6 and through crystallizer 7 back to the resin kettle 1. The crystallizer 7 is cooled to a temperature sufficient to cause the sorbic acid, meaning the trans, tran-hexa-2,4-dienoic acid, to crystallizer, such as 10° C. or so. The crystals collect in crystallizer 7, and the pre-cooler crystallizer can be disassembled at appropriate intervals to remove product. The solubility of the t,t-sorbic at the crystallizer temperature is very low, so that the concentration of t, t-sorbic in the reaction stream circulating through the resin bed is kept at a fairly low value, improving selectivity to sorbic acid. In addition to trans, trans-2,4-hexadienoic acid, small amounts of its stereoisomers are generally produced, possibly up to 5% or so. The isomers are trans-cis, cis-trans, and cis-cis, and possibly also position isomers in which the double bonds are in position other than 2,4. It happens that only the t,t-sorbic acid is amenable to crystallization under the described conditions. Other stereo isomers of hexa-2,4-dienoic acid are liquid at room temperature and fairly soluble in hydrocarbon solvents at temperature well below. room temperature. Since the acidic resin catalyst causes isomerization from one stereo form of sorbic acid to others, tending toward an equilibrium concentration, the recurrent acid contact and crystallization procedure provides a convenient method of effecting conversion of sorbic acid isomers to the desired t,t-sorbic acid. Also, it provides a convenient method of separating the desired isomer from its stereo isomers.

The apparatus illustrated in FIG. 1 is adapted to alternate heating and cooling stages for a reaction stream, with provision for the hot stream to be in contact with acidic resin for reaction, and for collection and filtration or other removal of product from the cold reaction stream. Other apparatus and procedures for effecting such multi-stage, cyclic operation can be employed if desired. The resin kettle 1 has provision for magnetic stirring by impeller 13. The kettle is a convenient reservoir to effect heating of the reaction stream, but other means can be employed to heat the moving stream enroute from the crystallizer to the resin bed, such as a continuously heated conduit line, or provision for faster heat input to the resin bed. The illustrated apparatus physically separates the acid contact stage from the crystallization stage. However, it is possible to conduct both stages in the same vessel. Thus a vessel like 1 can be employed but with means for both heating and cooling. The acidic resin can be placed in the vessel with the other components and heat applied to effect partial conversion of sorbic acid precursor to sorbic acid. The vessel can then be cooled to effect crystallization of sorbic acid, which can be separated by filtration. The filtrate is then subjected to further heating for reaction and cooling for crystallization cycles. However, such procedure may not be well adapted to keep the sorbic content of the reaction medium as low as it might be in a continuous procedure with physically separate stages. Moreover, the product sorbic crystals will be mixed with resin particles, unless provision is made for separating the resin particles prior to crystallization. This problem is avoided if a mineral or other acid is employed. Use of the same vessel would have some advantage in limiting the equipment required, but this advantage would be offset to some extent by poorer product purity, in particular with regard to contamination with acid or high boiling material.

The crystallization of sorbic acid is generally effected at temperatures in the range of about 0° C. to about 20° C. or so, but any temperature which is effective in the particular medium can be employed. Temperatures below 0° C. involve unnecessary costs, but can be used with solvents which do not freeze at such temperatures. Acetic acid freezes at 16°–17° C. so it is necessary to use higher temperatures with that solvent, such as 20° C. or slightly higher. Sorbic acid has very low solubility in cold water so temperatures over 20° C. may be used with aqueous solvents, and ordinary cooling water is often sufficient as the cooling medium to effect crystallization.

Figure 2:
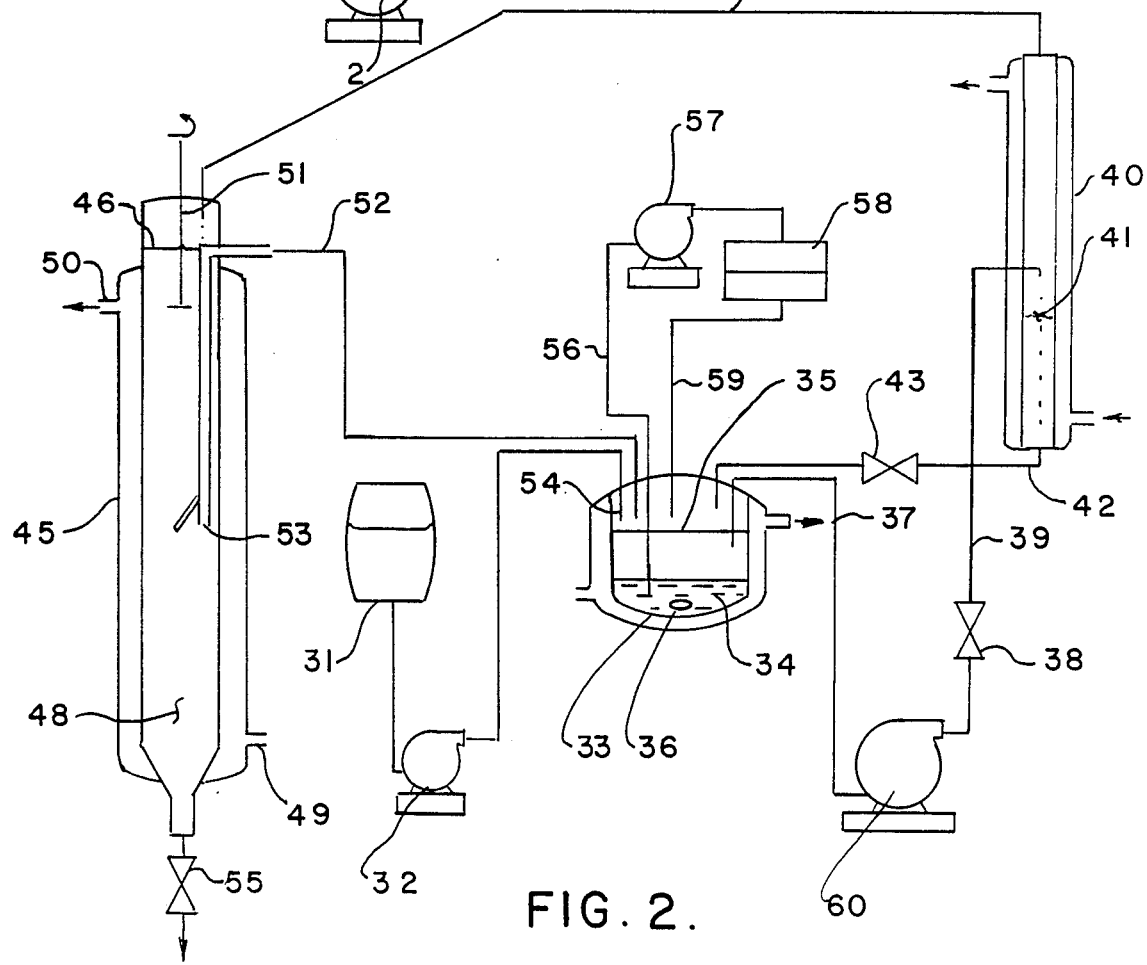
FIG. 2 illustrates an apparatus for effecting the reaction employing a solvent for the sorbic acid precursor which is not miscible with the aqueous acid catalyst utilized. The solvent serves as a carrier for the precursor and to extract the sorbic acid from the aqueous acid phase, and as a medium from which the sorbic acid is crystallized.

Another reactor-crystallizer apparatus is illustrated in FIG. 2. A lactone reservoir vessel 31 is connected by a line to pump 32 for addition of the lactone by a conduit to jacketed kettle 33. The kettle contains an aqueous acid phase 34 and an organic phase with organic solvent and lactone with surface 35. The kettle contains an impeller 36 for magnetic stirring, and in operation the phases are intermixed to some extent. Exit line 37 has its inlet located below surface 35 so that pump 60 can pump material from the kettle through control valve 38 and line 39 to a jacketed liquid separator 40. The separator 40 is generally filled with liquid in operation with a surface 41 between the lower aqueous phase and the upper organic phase. Conduit line 42 from the bottom of separator 40 leads through control valve 43 to kettle 33 where it terminates above surface 35. The heavier aqueous phase is returned through line 42 to the reaction kettle, and by proper setting of valve 43 it is possible to return mainly aqueous acidic phase and very little organic phase. The reaction stream exits from separator 40 through conduit line 44 to jacketed crystallizer 45. The crystallizer in operation will be filled with the liquid reaction stream with upper surface at 46, and sorbic acid crystals 48 will settle toward the bottom of the crystallizer. Coolant is circulated through the jacket of the crystallizer with inlet at 49 and outlet at 50. The crystallizer is provided with a stirrer 51. For return of liquid to the reaction kettle, conduit line 52 is provided, with inlet 53 well below the liquid level in the crystallizer and outlet 54 usually above the surface 35 in kettle 33. The crystallizer 45 is provided with an exit conduit through valve 55 to remove sorbic acid crystals for filtration. The crystallizer can optionally be one of various designs, for example, a crystallizer formed from sections 6 and 7 of FIG. 1 can be substituted for 45.

The reaction kettle 33 is provided with a carbon filtration system comprised of conduit line 56 through pump 57 to carbon filter 58 and return to the kettle through line 59. The filtration system is an optional component to provide means for removing contaminants from the system. The kettle 33 and separator 40 are illustrated with jackets with inlets and outlets for hot oil circulation.

In operation with the FIG. 2 system, the $\gamma$-vinyl-$\gamma$-butyrolactone or other precursor is continuously added to the reaction kettle and heated there in organic solvent in contact with aqueous mineral acid. There is continous removal of liquid from the kettle, principally the organic phase containing lactone reactant and sorbic acid product, which is pumped to the separator, with any aqueous phase being substantially completely returned to the kettle. In effect, the organic solvent in the separator extracts the sorbic acid from the aqueous phase. The organic part of the stream is conducted to the crystallizer, where cooling is effected to cause crystallization of the sorbic acid. The crystallization occurs in substantially the same way as in the crystallizer in FIG. 1. The crystallization is from an organic solvent in which sorbic acid is fairly soluble, so cooling is required to effect crystallization. Since the crystallization is from an organic solvent, the product is substantially free from acid contamination. As is the case in the FIG. 1 apparatus, the FIG. 2 system involves continuous crystallization and makes it feasible to have very low concentrations of sorbic acid in the reactant solution, thereby improving selectivity to sorbic acid. The concentrations of sorbic acid are generally below 5% by weight, often below 3% by weight, and will preferably be kept below 2% by weight, and the procedures herein are suitable for keeping sorbic acid concentrations below 2% by weight.

It will be recognized that many of the advantages of the illustrated continuous procedures can be obtained by various batch or modified batch or intermittent procedures conducted in a cyclic manner. However, the illustrated procedures have the convenience of permitting re-use of catalyst in normal operation without the need to separate it from product when product is separated by filtration or similar procedures. It will be recognized that intermittent addition of reaction components and removal of product can be practical in the illustrated systems, while the sorbic acid preparation and crystallization is still carried on in a continuous manner. While reaction and crystallization are continuously being effected it will be recognized that the reaction is primarily in the reaction zone with components present there, while the crystallization occurs primarily in the crystallization zone with components there, and that a given segment of the reaction stream may cycle between the zones, rather than continuously taking part in reaction and crystallization.

The procedures herein generally involve use of a solvent for the sorbic acid precursor, which also serves as a medium from which the sorbic acid crystallizes. Various liquids in which a sorbic acid precursor is soluble can be employed. In particular, a medium is desired in which sorbic acid has appreciable solubility at elevated temperatures, but relatively low solubility at lower temperatures, such as from about 0° C. to 20° C. or so. The range around 10° to 15° C. may be a convenient range for operation. Solvents in which sorbic acid has solubility less than 2% by weight, and preferably no more than 1 or 1.5% at the desired crystallization temperature will be particularly useful. Hydrocarbon solvents can be employed, for example isooctane or n-decane. Halogenated hydrocarbons can also be used, although the solubility of sorbic acid in chlorobenzene exceeds the optimum. Since some precursor preparations involve acetic acid, it may be convenient to use acetic acid as the crystallizing solvent, and other alkanoic acids can be used, particularly lower, liquid alkanoic acids. The main criterion for the liquid medium is that it serves as a crystallizing medium or solvent for the sorbic acid at a suitable crystallization temperature, ordinarily in the range of about 0° C. to 20° C.

The concentrations of reactants, catalysts and solvents can be selected to obtain desired reaction rates and selectivity to sorbic acid without excessive solvent for handling. Any amount of acid catalyst will have some effect, but to insure sufficient acid it is preferable to use at least an amount equimolar with the sorbic acid precursor in the reaction zone, although amounts ranging from 0.25 moles up to 5 moles or more per mole of precursor may be entirely satisfactory. With some acids the concentration can have a significant effect upon rates; for example, with hydrochloric acid, concentrated hydrochloric acid is preferred, such as about 36% hydrochloric acid, although dilute hydrochloric acid provides good rates when used in conjunction with cuprous ion. Various other acid or acidic catalysts as described in U.S. Pat. Nos. 4,022,822 and 4,158,741 can be utilized in the present invention with some degree of success. In general if the catalyst is effective for converting a precursor to sorbic acid, it can be utilized in the present invention. Effective catalysts which are solid and insoluble can be utilized like ion exchange resins, while aqueous liquid catalysts can be used like hydrochloric acid.

When the sorbic acid precursor is to be circulated for contact with ion exchange resin, it is desirable to have appreciable solubility in the carrier. For a two-phase system, it is not necessary to have the precursor very soluble in the organic solvent, and in fact the $\gamma$-vinyl-$\gamma$-butyrolactone precursor has relatively low solubility in hydrocarbon solvents and tends to concentrate in the aqueous phase where it is converted to sorbic acid. In a single phase system, at times it may be convenient to limit the precursor addition rate so as to avoid formation of two phases.

There is some improvement in selectivity to sorbic acid from use of relatively dilute solutions of precursor in solvent, as compared to more concentrated solutions, although concentrations from less than 1% to more than 20% or so by weight of precursor or to solubility limits, can be used. Gradual or incremental addition of precursor may be used to limit its concentration, possibly keeping it to less than 10% of the organic medium used, or possibly less than 5% or even near 2%. While recognizing that low concentrations improve selectivity, the concentration of precursor should be high enough to provide reasonable reaction rates and space velocities.

EXAMPLE 1

A mixture of 6-acetoxy-4-hexenoic acid and 4-acetoxy-5-hexenoic acid (3 grams) was slowly added over a 2.5 hour period to acetic acid (11.8 grams) at reflux over Amberlyat 15 ® resin (3 grams). Vapor phase chromatographic analysis showed a selectivity to sorbic acid isomers of 82% with an 82% mass balance. When the procedure was repeated, but with all of the acetoxyhexenoic acid mixture present initially, and with heating for one-half hour, the selectivity to sorbic acid was 75% with a 79% mass balance.

EXAMPLE 2

A mixture of acetoxyhexenoic acids (1.6 grams) and Amberlyst 15 resin (3 grams) in chlorobenzene (10 ml) was heated at 85° C. for 2.5 hours. The yield of sorbic acids was 72% with a material balance of 79%. When the procedure was repeated but with a one gram amount of sorbic acid initially charged along with the acetoxy-acids, the yield of sorbic acid declined to 51% with a 67% mass balance. The one-gram of sorbic acid from the original addition was substrated from the product in making the yield calculation.

EXAMPLE 3

A sample of sorbic isomers contained 36% trans, tran-2,4-hexadienoic acid 64% of other 2,4-hexadienoic acid isomers. It was heated at reflux in acetic acid (19 grams) with Amberlyst 15 ® resin (3 grams) for four hours. Vapor phase chromatography showed 71% trans, trans-2,4-hexadienoic acid and 21% of its stereo isomers, with a 95% mass balance. Thus the isomerization toward the desired isomer proceeded with good selectivity and a reasonable rate.

EXAMPLE 4

A quantity of γ-vinyl-γ-butyrolactone (6 grams) was added slowly (0.75 ml/15 minutes) to octane (30 grams) containing Amberlyst 15 ® resin (3 grams) at reflux. The reflux was continued for 1.25 hours after addition was complete. The selectivity to t,t-sorbic was 46% at 98% conversion. The product and solvent were removed, and the resin catalyst was used in a repetition of the procedure, with 54% selectivity at 94% conversion; additional repetitions gave 68% selectivity at 88% conversion, and 51% selectivity at 77% conversion. The average selectivity to t,t-sorbic acid for the four runs was 55%.

EXAMPLE 5

The reactor-crystallizer apparatus of FIG. 1 was utilized, employing 40 grams of Amberlyst 15 ® resin, which had been washed with acetic acid, followed by octane. A 20 gram amount of γ-vinyl-γ-butyrolactone was slowly added (0.2 ml/minute) to hot octane in the resin kettle 1. The octane was circulated through the resin bed 4 to the crystalizer and back to the resin kettle at about 15 ml/minute. The temperature in the resin bed was about 90°–95° C. and the crystallizer was kept at about 5°–10° C. After three hours, crystalline t,t-sorbic acid was removed from the crystallizer and analyzed. The yield was 68%. Upon repetition of the procedure, employing the same sample of catalyst resin, yields of 83% and 81% were obtained. It can be seen that the yield in this continuous crystallization procedure was considerably improved over that in Example 4.

EXAMPLE 6

The resin from Example 5 was weshed with acetic acid and then used in repetitions of the procedure, but using decane as solvent. After an initial run, yields of 87%, 87%, 83% and 82% were obtained in repetitions.

EXAMPLE 7

Utilizing the apparatus substantially as illustrated in FIG. 2, γ-vinyl-γ-butyrolactone was reacted in a two-phase system employing isooctane as solvent and CuCl and hydrochloric acid as catalyst. A 3 gram amount of cuprous chloride was used with 29 grams of 25% hydrochloric acid. The amount of isooctane was 325 ml, and the reaction temperature was 86° C., while cooling was employed to effect crystallization of the sorbic acid product. Four runs were made in series, each employing 22.4 grams of the lactone, with results as reported in Table 1. The cumulative molar ratio of lactone to hydrochloric acid changed from 1/1 to 4/1 over the four runs, with no strong effect on results.

TABLE 1

| Run # | Lactone (grams) | Yield % | Conc. Sorbic end of run | Addition* time, hrs. | Molar Ratio lactone/HCl |
|---|---|---|---|---|---|
| 1 | 22.4 g | 81 | 1.4% | 3.75 | 1/1 |
| 2 | " | 93 | 1.0% | " | 2/1 |
| 3 | " | 88 | .9% | " | 3/1 |
| 4 | " | 84 | 1.4% | " | 4/1 |

*Runs continued for 1 hour after addition

The apparatus used was like that in FIG. 2 except that a crystallizer formed of parts like 6 and 7 of FIG. 1 was substituted for crystallizer 45 of FIG. 2.

It can be seen that the procedure using liquid aqueous acid can involve use of a water immiscible solvent for contact with the aqueous acid and extraction of the sorbic acid product from the aqueous acid, as well as a medium from which the sorbic acid is crystallized.

EXAMPLE 8

A mixture of acetoxyacids was employed as the sorbic acid precursor in a procedure in the apparatus illustrated in FIG. 1. The acetoxyacids were a mixture of 6-acetoxy-4-hexenoic acid and 4-acetoxy-5-hexenoic acids. The reactor was charged with 161 g of a mixture of acetic acid and nonane (¼, v/v) and Amberlyst 15 resin (25 g). When the temperature in the reactor reached 117° addition of the acetoxyacids (39 g) was started. After three hours the addition was complete and after 4.5 hours heating was stopped. A 30% yield of t,t-sorbic was obtained. Three additional experiments were carried out and the yields of sorbic acid were 64, 72 and 70% respectively. The yields reported in this example are based upon the amount of acetoxyacids added to the reactor, without taking into account any which had not reacted and would be subject to recovery, and, of course, are based only upon trans, trans-sorbic acid, rather than including all stereo isomers of sorbic acid. It appears that the yields were adversely affected by the release of acetic acid from the acetoxyacid in the process, resulting in more acetic acid in the solvent and higher than desirable solubility of sorbic acid in the solvent mixture. If provisions are taken for removal of excess acetic acid, yields comparable to those from γ-vinyl-γ-butyrolactone will be obtainable. The excess acetic acid could be removed by heating the reaction stream after exit from resin column 4 to effect distillation of part or all of the acetic acid, so that all but a very small part of the sorbic acid product would be separated by crystallization in the crystallizer. Acetic acid forms an aceotrope with octane, making it possible to remove appreciable amounts of acetic acid at about 95° C. With higher alkanes, the acetic acid will distill at lower temperatures than the alkane. Acetic acid appears to have a beneficial effect or activity of the ion exchange resin so that it may be useful to return a portion of the acetic acid to the resin kettle, or to the circulating stream in advance of resin, column 4.

What is claimed is:

1. The process of preparing sorbic acid which comprises contacting sorbic acid precursor in a reaction medium at elevated temperature with an acid catalyst effective for converting such precursor to sorbic acid to convert part of the precursor present to sorbic acid, conducting the reaction medium to a cooling stage to effect crystallization of sorbic acid, and recycling the reaction medium, from which sorbic acid has been removed, to contact the acid at elevated temperature, with such crystallization being from organic solvent, said process wherein the rates of reaction and crystallization, and reaction and crystallization times are such that the sorbic acid concentration in the reaction medium is maintained at an average value no greater than 2% by weight.

2. The process of claim 1 in which the sorbic acid is crystallized from an organic solvent therefor at a temperature below 25° C.

3. The process of claim 1 in which sorbic acid is produced in a continuous process with recycling of the precursor between a heating stage for reaction and a cooling stage for crystallization and separation of sorbic acid.

4. The process of claim 3 in which the sorbic acid precursor is replenished by additional precursor during the process.

5. The process of claim 3 in which isomerization of 2,4-hexadienoic acids occurs toward an equilibrium mixture of stereoisomers and trans,trans-sorbic acid is selectively crystallized from the mixture.

6. The process of claim 1 in which the catalyst is aqueous acid and the sorbic acid is crystallized from organic solvent.

7. The process of claim 1 in which the sorbic acid precursor in an organic solvent which is water immiscible is contacted at elevated temperature with aqueous acid and sorbic acid in such organic solvent is then removed from such aqueous acid, and crystallization of sorbic acid is then effected by cooling the organic solvent.

8. The process of claim 7 in which organic solvent containing sorbic acid precursor is continuously cycled between the aqueous acid and a cooling-crystallization stage.

9. The process of claim 1 in which the sorbic acid precursor is selected from γ-vinyl-γ-butyrolactone, acyloxy-hexenoic acids and polyester of 3-hydroxy-4-hexenoic acid.

10. The process of claim 1 in which the sorbic acid precursor is γ-vinyl-γ-butyrolactone.

11. The process of claim 1 in which the sorbic acid precursor is a mixture of 6-acetoxy-4-hexenoic acid and 4-acetoxy-5-hexenoic acid.

12. The process of claim 1 in which the acid catalyst is an aqueous mineral acid.

13. The process of claim 1 in which the acid catalyst is hydrochloric acid.

14. The process of claim 1 in which the acid catalyst is a cation exchange resin.

15. The process of claim 1 in which a hydrocarbon solvent is employed.

16. The process of claim 1 in which acetic acid is employed as a solvent.

17. The process of claim 1 in which an organic solvent is employed and the temperature in the reaction zone is in the range of 60° to 140° C. and crystallization is effected by cooling to a temperature below 20° C.

18. The process of claim 17 in which the concentration of sorbic acid precursor in the organic solvent is kept below 10% by weight.

19. The process of preparing sorbic acid from a sorbic acid precursor by contact with acid, the improvement which comprises crystallizing sorbic acid from organic solvent during the preparation so that the concentration of sorbic acid in the medium contacting acid is maintained at a value no greater than 2% by weight.

20. A process for preparing sorbic acid in which a sorbic acid precursor in an organic solvent contacts an acid catalyst at elevated temperature to effect conversion of a small fraction of said precursor to sorbic acid, a portion of solvent containing sorbic acid is removed from contact with acid catalyst, and sorbic acid is crystallized from the solvent.

21. A process for preparing sorbic acid in which a sorbic acid precursor in an organic solvent contacts an aqueous acid to effect conversion of a small fraction of said precursor to sorbic acid, a portion of solvent containing sorbic acid is removed from contact with said aqueous acid, and sorbic acid is crystallized from the solvent.

* * * * *